United States Patent
Brown et al.

(10) Patent No.: US 6,432,421 B1
(45) Date of Patent: Aug. 13, 2002

(54) EMOLLIENT COMPOSITIONS WITH POLYETHYLENE BEADS

(75) Inventors: James S. Brown, Gilbert; James H. Brown, Scottsdale, both of AZ (US)

(73) Assignee: International Flora Technologies, Ltd., Gilbert, AZ (US)

( * ) Notice: Subject to any disclaimer, the term of this patent is extended or adjusted under 35 U.S.C. 154(b) by 0 days.

(21) Appl. No.: 09/547,482

(22) Filed: Apr. 12, 2000

(51) Int. Cl.⁷ .................................................. A61K 7/00
(52) U.S. Cl. ....................................... 424/401; 424/489
(58) Field of Search .......................... 424/401, 59, 489; 514/845, 847

(56) References Cited

U.S. PATENT DOCUMENTS 5,308,526 A * 5/1994 Dias et al. ................... 252/125
5,753,245 A * 5/1998 Fowler et al. .............. 424/401

* cited by examiner

Primary Examiner—Jose' G. Dees
Assistant Examiner—Konata M George
(74) Attorney, Agent, or Firm—The Halvorson Law Firm

(57) ABSTRACT

An emollient composition comprising at least 5–30% by weight polyethylene, 0–60% by weight petrolatum, and 0–50% octyl palmitate. These emollient compositions may be used as emollient carriers for various materials, such as fragrances and pigments or dyes, to be externally applied to the skin. These emollient compositions may be formed into particulate shapes, such as spheres, for subsequent use in cosmetic products.

20 Claims, No Drawings

EMOLLIENT COMPOSITIONS WITH POLYETHYLENE BEADS

FIELD OF THE INVENTION

The present invention relates to emollient compositions for use in cosmetic, personal care and pharmaceutical preparations and more particularly to such emollient compositions partially comprising polyethylene, petrolatum, and octyl palmitate in a generally solid spherical form (beads) and processes for their preparation.

BACKGROUND

Emollients tend to be bland, fatty, oleaginous substances which may be applied locally to the skin, mucous membranes, or abraded tissue. One of the benefits of emollients is their ability to exclude water-soluble irritants, air, and air-borne bacteria when a layer of emollient is present. At the present, there are numerous ingredients which function as emollients in a wide variety of products, and which ingredients may act in subtly different ways. For example, certain emollients sit on the surface of the skin and serve to impede water loss from the skin. Such ingredients are generally comprised of large molecules that form a hydrophobic barrier to help prevent water from leaving the surface of the kin. Examples of such emollients are lanolin, mineral oil, silicon derivatives and petroleum jelly.

A chief use of emollients is to provide vehicles for lipid-soluble drugs (as in balms, ointments and alcohol-based liniments). Although it has often been suggested that such emollient vehicles facilitate the transport of such drugs through the skin, it has been found that when the oil:water partition coefficient is greater that 1.0, the penetration of lipid-soluble drugs tends to be impeded. Emollient substances are commonly employed in cleansing and antiphlogistic creams and lotions. Compound ointment bases, creams, and other medical applications are also general areas of use for emollients. Amongst the more common emollient materials are castor oil, corn oil, cottonseed oil, rose water ointment, apricot kernel oil, avocado oil, grape seed oil, hazelnut oil, olive oil, sesame oil, theobroma oil, almond oil, myristyl alcohol, and recently other natural oils such as jojoba oil.

Fatty alcohols are also used as emollients. They are said to be less sticky and less heavy that many other fatty materials, such as the fatty acids, and are frequently used to improve the viscosity and stability of lotions and creams. They also have utility in reactive hair dying and perming products. Examples of fatty alcohols that find use in the field of cosmetics and personal care products are cetyl alcohol, lauryl alcohol, stearyl alcohol and oleyl alcohol.

Additional examples of emollients are fatty esters. One of the best qualities of fatty esters is that they do not feel as oily to the touch as some other types of emollient fatty ingredients. Examples include isopropyl palmitate, isopropyl myristate and glyceryl stearate.

An important emollient is jojoba oil that is derived from the seed of the species *Simmondsia chinensis*. Jojoba oil is seed oil with excellent skin feel. The oil is composed almost exclusively of wax esters, with little or no triglycerides present. A major portion of the production of jojoba oil is used by the cosmetic industry as an emollient in a variety of products.

One of the problems with typical emollients is that the emollient itself provides a wet or oily feel to the applied areas. This can lead to an uncomfortable feeling or appearance to the user, which is very important in the cosmetic and pharmacological industry. An additive for cosmetic, personal car and topical treatment (medicament) products has been marketed under the name of "Confetti"™ AL with allantoin, and ConfettiT™ EA, MT, PA, RG and SG (identifying the color of the material). This material is advertised as decorative microcapsules that contribute beneficial moisturizing and delivery of alcohol soluble ingredients to the skin. Confetti is advertised as having a good balance of structural integrity and rub-in characteristics, rubbing into the skin completely without any extra pressure. The Material Safety Data Sheets (MSDS) on ConfettiT™ products identifies them as containing a natural oil (e.g., coconut oil, tocopheryl acetate, retinyl palmitate), propylene glycol, synthetic beeswax, petrolatum, allantoin, PVM/MA Decadiene crosspolymer and benzophenone, as well as pigments and/or dyes.

SUMMARY OF INVENTION

The present invention describes a very effective emollient composition for use in personal care, cosmetic and pharmaceutical products and a novel method of producing that composition. The composition is essentially solid at room temperature and can be provided in various shapes and sizes (especially as spheres). The composition can be produced from a combination of polyethylene, petrolatum and octyl palmitate. Tints, fragrances and various other additives may be added to the composition to provide additional functionality and benefits.

The emollient compositions according to the present invention preserve an excellent skin feel and also increase the range of applications for cosmetic compositions by providing an emollient with a novel composition. Furthermore, when provided in a solid feel form, such as spherical particles, the emollient composition of the present invention can provide a noticeable scrubbing or dermal abrasive action. The emollient compositions of the present invention comprise polyethylene, petrolatum and octyl palmitate as described herein. Preferably the amount of the polyethylene will be from about 5–30% by weight of the composition, the amount of the petrolatum will be from about 0–60% by weight of the composition, and the amount of the octyl palmitate will be from 0–85% by weight of the composition, with any balance being the pigment or other additives. An especially preferred emollient composition will be as follows:

| Ingredient | % by weight |
| --- | --- |
| Polyethylene | 15 |
| Petrolatum | 35 |
| Octyl Palmitate | 50 |

Other emollients may be blended, mixed or dissolved with the basic emollient compositions described above.

The novel features that are considered characteristic of the invention are set forth with particularity in the appended claims. The invention itself, however, both as to its structure and its operation together with the additional object and advantages thereof will best be understood from the following description of the preferred embodiment of the present invention. Unless specifically noted, it is intended that the words and phrases in the specification and claims be given the ordinary and accustomed meaning to those of ordinary skill in the applicable art or arts. If any other meaning is intended, the specification will specifically state that a special meaning is being applied to a word or phrase. Likewise, the use of the words "function" or "means" in the Description of Preferred Embodiments is not intended to indicate a desire to invoke the special provision of 35 U.S.C. §112, paragraph 6 to define the invention. To the contrary, if the provisions of 35 U.S.C. §112, paragraph 6, are sought to be invoked to define the invention(s), the claims will specifically state the phrases "means for" or "step for" and a function, without also reciting in such phrases any structure, material, or act in support of the function. Even when the claims recite a "means for" or "step for" performing a function, if they also recite any structure, material or acts in support of that means of step, then the intention is not to invoke the provisions of 35 U.S.C. §112, paragraph 6. Moreover, even if the provisions of 35 U.S.C. §112, paragraph 6, are invoked to define the inventions, it is intended that the inventions not be limited only to the specific structure, material or acts that are described in the preferred embodiments, but in addition, include any and all structures, materials or acts that perform the claimed function, along with any and all known or later-developed equivalent structures, materials or acts for performing the claimed function.

DETAILED DESCRIPTION OF PREFERRED EMBODIMENTS

The present invention describes a very effective emollient composition for use in personal care, cosmetic and pharmaceutical products that can be produced from a combination of polyethylene, petrolatum and octyl palmitate.

The emollient composition of the present invention comprises a family of emollients that have melting points that range from 30–80° C. At room temperature (~20° C.), this family of emollients varies from pourable liquids, to soft creams, to pasty waxes, to a brittle hard material. The composition of the emollient of the present invention may be blended with different melting point components within the family to form products with selected melting points and specific physical properties or feel. These compounds, whether used pure or when combined with other carrier and vehicle components (including other emollients or binders) can form excellent carrier and vehicles for delivery of compositions for use in the cosmetic, personal care and/or pharmaceutical field, including the cosmeceutical field where cosmetic compositions also provide pharmaceutical or other therapeutic benefits. Typical materials with which the compound may be blended in accordance with the practice of the present invention include, but are not limited to, cosmetic oils and waxes, both natural and synthetic, including hydrogenated or partially hydrogenated oils, silicon oils, mineral oils, long chain esters, vitamins (especially vitamin E), long chain fatty acids, alcohols, cosmeceuticals, pigments, botanical extracts, esters and ethers, dimers, trimers, oligomers, and polymers, and the like. These blended compositions may of course be combined with the active ingredients intended to be delivered by the composition used in the present invention.

The dry-feel compositions of the present invention may be applied to the skin as particulate materials, usually in a cosmetic, personal care, cosmeceutical or pharmaceutical composition. The processes of making the particles generally provides them as spherical or oblong particles, but they may be shaped by pressing, molding, spray drying, atomization or other stresses to provide shape particles, including platelets. The compositions have particular properties that renders them especially suitable for use in fragrance dispensing compositions and topical applications, and those properties include their spreadability, emolliency, non-volatility, lack of color and lack of odor. The lack of odor is mildly important in pharmaceutical applications, but is viewed as particularly essential in the provision of fragrances; Perfume and cosmetic providers have extremely rigid standards on non-essential odor contribution in their products.

By skillful blending, a composition may be prepared that melts at slightly below skin temperature. When formed into spherical particles and rubbed into the skin, these spherical particles disappear into the skin. Indeed they soften, melt and are absorbed into the surface of the skin where they deposit a layer of the fragrance. The polyethylene is non-volatile and forms an imperceptible film on the skin that slows down the release of the fragrance. These compositions, being low in odor and superior skin emollients, provide an excellent carrier and delivery system for fine fragrances.

Spheres formed from the present invention that contain fragrance or perfume can be incorporated into a larger variety of cosmetic and personal care products for the purpose of providing emolliency to the skin. At the same time, these fragrances bearing spheres serve to deliver fragrance oils to the skin. Traditional methods of fragrance delivery utilize fragrance oils incorporated in alcohol, typically ethyl alcohol. These traditional carriers of fragrance oils are, by definition Volatile Organic Compounds (VOC's) that evaporate into the air after being applied to the skin. The present invention provides a method to deliver fragrance oils to the skin and minimize VOC emissions.

Polyethylene is an excellent carrier of fragrance oils, especially when combined with petrolatum and octyl palmitate. As fragrance oil carriers, they are not prone to the development of rancidity or other unpleasant odors, resulting in delivery of the fragrance compound to consumers in a form as near that created by the perfumer as possible. They physical form of the compound according to the present invention can be adjusted to accommodate any type of consumer product application desired. As an example, fragrance oils can be incorporated in liquid, pourable versions that at ambient temperatures can be used by a consumer in a manner similar to the traditional use of alcohol and fragrance oil blends. The compounds of the present invention containing fragrance oil can be formed into spheres and these spheres subsequently incorporated into cosmetic bases with a wide range of physical and chemical properties. In this spherical form (as a discontinuous phase or dispersed phase), the compounds serve to minimize the level of contact of the fragrance oil with the cosmetic base (as a continuous phase). This is a desirable effect when the fragrance oil contains components that are not compatible with the cosmetic base, or vice versa. The particles are usually present as a dispersion of the particles in a flowable continuous phase carrying medium that is not a solvent for said particles. By flowable, it is meant that the carrying medium may be a liquid, higher viscosity fluid (such as a gel) or other material that can be spread by manual pressure in application to the skin. The aspect of non-dissolvability of the particles within the carrying medium is desirable so that the particles do not dissolve into the carrying medium and destroy the dispersed nature of the combination. The combination may use a solvent carrier, if it is acceptable in the particular use to have the particles dissolved and carried as a solute.

The emollient compositions of the present invention comprise polyethylene, petrolatum and octyl palmitate as described herein. The emollient composition should have a minimum of at least about 5% by weight of the polyethylene, at least 0% by weight of the petrolatum, and at least 0% by weight of the octyl palmitate. Preferably the amount of the polyethylene will be from about 5–30% by weight of the composition, the amount of the petrolatum will be from about 0–60% by weight of the composition, and the amount of the octyl palmitate will be from 0–85% by weight of the composition, with any balance being the pigment or other additives. An especially preferred emollient composition will be as follows:

| Ingredient | % by weight |
|---|---|
| Polyethylene | 15 |
| Petrolatum | 35 |
| Octyl Palmitate | 50 |

Other emollients may be blended, mixed or dissolved with the basic emollient compositions described above.

Individual compositions can be warmed to just above their melting point, a fragrance oil incorporated, and then the molten blend poured into a jar or other dispersing package where it will solidify upon cooling. The consistency of the blended product in the container can be adjusted to facilitate its application to the skin by use of the fingers or by a method of application using the packaging material.

Fragrance oils are normally compounded to exhibit a range of natural volatility. The compositions of the present invention function as "fixatives" that help control the premature release of volatile components of fragrance oils. The "fixative" function can be manipulated for optimum compatibility with different fragrance oils by skillful blending to produce different melting points. The compositions of the present invention are utilized as oxidatively stable carriers of fragrance oils and are capable of being modified or blended in different ratios to arrive at the optimum "skin feel" and "fixative" function that might be desired.

The term emollient carrier reflects the fact that the at least three materials described above form a component which may be mixed, blended dispersed, emulsified or dissolved with other materials, is itself an emollient, and may be a carrier for these other materials. Typical additional materials which may be combined with the emollient carrier of the invention may include, but are not limited to, additional emollients, oils, fragrances, pigments (e.g., inorganic pigments, organic pigments, dyes), medicaments (e.g., antimicrobial agents, antibacterial materials, antifungal materials, anti-inflammatory agents, transcutaneously administered drugs, etc.), emulsifying agents, stabilizing agents, binders, fillers, antiagglomerants (especially where powders are present in the emollient carrier, as with certain cosmetics), ultraviolet radiation absorbers (as in the formulation of sunblocks and sunscreens), insect repellants (e.g., DEET), pheromones, enzymes, barrier materials (e.g., resins to prevent contact with toxins such as plant irritants), and the like. These materials may be present in essentially any desired amount, but usually within the range of from 0.1% by weight of total composition up to 95% by weight of total composition, with 0.1 to 50% by weight preferred, and 0.5% to 25% by weight being more preferred.

A process for producing an emollient may comprise the steps of:

a) providing a composition comprising polyethylene, b) adding a petrolatum, to said composition, and c) adding octyl palmitate to produce an emollient.

In preparing the emollient composition, refined polyethylene is introduced into an appropriate vessel (capable of excluding air) equipped with stirring and means of heating and cooling. The amount of polyethylene used being from about 5% to about 30% by weight of the composition. The petrolatum is then added with the amount of petrolatum used being from about 0% to about 60% by weight of the composition. Finally, octyl palmitate is added with the amount of octyl palmitate used being from about 0% to about 50% by weight of the composition. The reactor is sealed and heat is applied to bring the temperature of the reaction mixture to about 70–75° C. When the temperature has reached 70–75° C., a first addition of additive or other active ingredient is made. The amount added ranges from about 0% to about 50% by weight of the emollient composition with about 0.3–25% being preferred. Heating is discontinued but no cooling is applied.

Following the previously described procedure, the following formulas detail examples of the preparation of different batches of emollient compositions.

| Formula 1. | |
|---|---|
| Composition | 90 grams |
| Fragrance Oil | 10 grams |

This blend of the composition of the present invention and fragrance oils melts at approximately skin temperature and if desired, can be formed into small spheres for direct application to the skin or for incorporation in other cosmetic base formulas.

| Formula 2. | |
|---|---|
| Composition | 60 grams |
| Fragrance Oil | 40 grams |

This blend is liquid at ambient temperature and can be applied to the skin in the manner of traditional perfumes.

| Formula 3. | |
|---|---|
| Composition | 85 grams |
| Fragrance Oil | 15 grams |

This blend melts at just above skin temperature and is suitable for direct application to the skin or can first be formed into spheres for subsequent incorporation in other cosmetic bases.

| Formula 4. | |
|---|---|
| Composition | 45 grams |
| Fragrance Oil | 55 grams |

This blend has the consistency of a non-flowing semi-solid paste. Application of stronger levels of fragrance that are long lasting on the skin are possible utilizing this carrier system.

| Formula 5. | |
|---|---|
| Composition | 90 grams |
| Fragrance Oil | 9 grams |
| FD&C Red #40 | 1 gram |

This blend is a non-flowing semi-solid that is appropriate for direct application to the skin. A pigment has been added to increase the visual impact of the invention.

| Formula 6. | |
|---|---|
| Composition | 88 grams |
| Fragrance Oil | 10 grams |
| Ultramarine Blue | 2 grams |

This blend includes a pigment selected for stability in high pH (greater than 8.0) aqueous cosmetic bases. This blend is suitable for formation into spheres and subsequent incorporation in cosmetic bases such as shower gels, facial creams, eye creams, body lotions, etc. The pigment has been selected for its compatibility with aqueous cosmetic bases.

Other compatible cosmetic ingredients may be added to any of the above formulas to achieve different melting points, flow characteristics, water resistance, and the like. Examples of other cosmetic ingredients that may be suitable for addition to the above formulas are beeswax, castor wax, carnauba wax, vegetable oils, partially hydrogenated vegetable oils, surfactants such as Tween 60™ or Tween 80™, silicone preparations, fatty alcohols, fatty acids and fatty acid esters, alpha and beta hydroxy acids, vitamins (such as vitamin E, vitamin E acetate, vitamin A palmitate, beta carotene, vitamin C, and the like), herbal extracts, alpha-bisabolol, conjugated linolenic acid (CLA), antioxidants such as tocopherols or mixed natural tocopherols, other antioxidants, such as BHA or BHT. Pigments may also be added to any of the above to create unique visual effects.

These and other aspects of the invention will be further described and enabled in the practice of the following, non-limiting examples.

EXAMPLES

Example 1

A moisturizer composition, in the form of the dry-feel emollient compositions of the present invention is spherical particle form, was prepared as follows. The following distinct phases or compositions were used in the preparation.

| | |
|---|---|
| Dionized water | 57.85 |
| Disodium ethylenediaminetetraacetic acid | 00.03 |
| Carbopol ™ 981 (Carbomer, B.B. Goodrich) | 00.25 |
| A. Glycerine 96% (Dow) | 05.00 |
| Polyglycol 1450 (PEG) (Dow) | 03.50 |
| Sorbitol 70 | 03.00 |
| Methylparaben (USP) | 00.20 |
| Germall 115 (Imidazolidinyl urea, Sutton) | 00.10 |
| Sodium Dehydroacetate | 00.05 |
| B. Deionized water | 05.00 |
| Triethanolamine | 00.70 |
| C. Composition | 08.10 |
| Softisan 100 (hydrogenated coco-glycerides, Huls) | 02.00 |
| Jojoba oil (refined grade, | 03.00 |

-continued

| | |
|---|---|
| International Flora Technologies) | |
| Lexeul 561 (glyceryl stearate and PED-100 Stearate, Inolex ™) | 02.50 |
| Shea Butter (Tri-K) | 01.50 |
| SF-1256 Fluid (Cyclomethicone, GE) | 01.50 |
| Pristerene 4911 (stearic acid, unichema) | 02.20 |
| Vitamin E acetate (tocopherol acetate, Roche) | 00.20 |
| Propylparaben, USP | 00.10 |
| D. Vitamin A palmitate with vitamin B-3 (Roche) | 00.20 |
| Fragrance, (Shaw Mudge M-7323) | 00.20 |
| F. Particulate emollients with 5% by weight B-carotene | 03.00 |

The water of phase A was heated to 800° C. Using high speed propeller agitation, the Carbopol 981 was sprinkled into the A phase. Once all of the Carbomer has been wetted out, mixing was continued for 15–20 minutes at 75° C. The remaining ingredients of phase A were then added. The ingredients of phase B were combined and then added to the combined phase A with medium propeller agitation. Phase C was heated to 75° C. with medium propeller stirring then added to the combined phases A and B with medium propeller stirring at 75° C. for 15 to 20 minutes. The mixture was cooled to 45° C. with stirring. Phase D was added to the blended phases A, B, and C with medium propeller stirring for 15–20 minutes until the mixture appeared to be uniform. The batch was cooled to 30° C. and phase E was blended in with slow sweep agitation until the mixture appeared to be uniform.

Example 2

An aqueous gel system of suspended solid emollient particles according to the present invention was prepared as follows. The following distinct phases or compositions were used in the preparation.

| | |
|---|---|
| A. Dionized water | 90.29 |
| Disodium ethylenediaminetetraacetic acid | 00.03 |
| Carbopol ™ 981 (Carbomer, B.B. Goodrich) | 00.50 |
| b. Propylene glycol, USP | 03.00 |
| Propylparaben, USP | 00.05 |
| Methylparaben (USP) | 00.25 |
| Germall 115 (Imidazolidinyl urea, Sutton) | 00.25 |
| Sodium Dehydroacetate | 00.03 |
| C. Jojoba Wax PEG-120 esters | 00.30 |
| dl-Panthenol | 00.50 |
| Lubrajel ™ MS (polyglycolmethacrylate, Guardian) | 01.00 |
| D. Triethanolamine | 00.80 |
| E. Particulate emollients with 5% by weight B-carotene | 03.00 |

The Carbopol was dispersed into the water of phase A with high speed propeller mixing and heated to 70° C. The EDTA was added with propeller agitation until dissolved. The ingredients of phase B were added into phase A while mixing at 65–70° C. Phase C was added into this resulting mixture with moderate propeller agitation. The batch was force cooled, and then with moderate sweep agitation, phase D was added to the batch. Adjustment of the pH to between about 6.8–7.2 was useful. The particulate emollient system of the invention was blended in with sweep agitation.

This example could be repeated easily with the Vitamin E acetate replaced with corresponding amounts of botanicals or other additive such as Vitamin C, calendula, ginko biloba, and the like.

In use, the emollient composition according to the present invention is provided in a contain suitable to the particular form the emollient occurs. An amount of emollient composition is applied to a portion of the skin that is to be moisturized. The emollient composition is then worked into the skin by gently rubbing the emollient composition with a hand or finger surface, using enough pressure to at least coat the surface of the skin being moisturized. When the emollient composition is provided in a generally solid feel form, preferably a substantially spherical form, the emollient composition should be worked into the skin until it effectively disappears to the touch.

The following list of cosmetic category codes identifies fields of use for the cosmetic emollient compositions and carriers of the present invention.

TABLE 1-2

FDA cosmetic category codes

| | |
|---|---|
| 01. | Baby products. |
| A. | Baby shampoos |
| B. | Lotions, oils, powders and creams |
| C. | Other baby products |
| 02. | Bath preparations |
| A. | Bath oils, tablets and salts |
| B. | Bubble Baths |
| C. | Bath capsules |
| D. | Other bath preparations |
| 03. | Eye makeup preparations |
| A. | Eyebrow pencil |
| B. | Eyeliner |
| C. | Eye shadow |
| D. | Eye lotion |
| E. | Eye makeup remover |
| F. | Mascara |
| G. | Other eye makeup preparations |
| 04. | Fragrance preparations |
| A. | Cologne and toilet waters |
| B. | Perfumes |
| C. | Powders (dusting and talcum, excluding aftershave talc) |
| D. | Sachets |
| E. | Other fragrance preparations |
| 05. | Hair preparations (non-coloring) |
| A. | Hair conditioner |
| B. | Hair spray (aerosol fixatives) |
| C. | Hair straighteners |
| D. | Permanent waves |
| E. | Rinses (non-coloring) |
| F. | Shampoos (non-coloring) |
| G. | Tonics, dressings, and other hair grooming aids |
| H. | Wave sets |
| I. | Other hair preparations |
| 06. | Hair coloring preparations |
| A. | Hair dyes and colors (all types requiring caution statements and patch tests) |
| B. | Hair tints |
| C. | Hair rinses (coloring) |
| D. | Hair shampoos (coloring) |
| E. | Hair color sprays (aerosol) |
| F. | Hair lighteners with color |
| G. | Hair bleaches |
| H. | Other hair coloring preparations |
| 07. | Makeup preparations (not eye) |
| A. | Blushers (all types) |
| B. | Face powders |
| C. | Foundations |
| D. | Leg and body paints |
| E. | Lipstick |
| F. | Makeup bases |
| G. | Rouges |
| H. | Makeup fixatives |
| I. | Other makeup preparations |
| 08. | Manicuring preparations |
| A. | Basecoats and undercoats |
| B. | Cuticle softeners |
| C. | Hair creams and lotions |
| D. | Nail extenders |
| E. | Nail polish and enamel |
| F. | Nail polish and enamel removers |
| G. | Other manicuring preparations |

TABLE 1-2-continued

FDA cosmetic category codes

| | |
|---|---|
| 09. | Oral hygiene products |
| A. | Dentifrices (aerosol, liquid, pastes and powders) |
| B. | Mouthwashes and breath fresheners (liquids and sprays) |
| C. | Other oral hygiene products |
| 10. | Personal cleanliness |
| A. | Bar soaps and detergents |
| B. | Deodorants (underarm) |
| C. | Douches |
| D. | Feminine hygiene deodorants |
| F. | Other personal Cleanliness products |
| 11. | Shaving preparations |
| A. | Aftershave lotion |
| B. | Beard softeners |
| C. | Men's talcum |
| D. | Preshave lotions (all types) |
| E. | Shaving cream (aerosol, brushless and lather) |
| F. | Shaving soap (cakes, sticks, etc.) |
| G. | Other shaving preparations products |
| 12. | Skin care preparations (creams, lotions, powder and sprays) |
| A. | Cleansing (cold creams, cleansing lotions, liquids and pads) |
| B. | Depilatories |
| C. | Face and neck (excluding shaving preparations) |
| D. | Body and hand (excluding shaving preparations) |
| E. | Foot powders and sprays |
| F. | Moisturizing |
| G. | Night |
| H. | Paste masks (mud pacts) |
| I. | Skin fresheners |
| J. | Other skin products |
| 13. | Suntan preparations |
| A. | Suntan gels, creams and liquids |
| B. | Indoor tanning preparations |
| C. | Other suntan preparations |

The preferred embodiment of the invention is described above in the Description of Preferred Embodiments. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s). The foregoing description of a preferred embodiment and best mode of the invention known to the applicant at the time of filing the application has been presented and is intended for the purposes of illustration and description. It is not intended to be exhaustive or to limit the invention to the precise form disclosed, and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated.

What is claimed:

1. A composition comprising solid particles comprising polyethylene, petrolatum and octyl palmitate, said solid particles carrying an active ingredient selected from the group consisting of fragrances, vitamins, medicaments, botanical extracts, and ultraviolet radiation absorbers, wherein the polyethylene, petrolatum and octyl palmitate are blended, or dissolved, in each other.

2. The composition of claim 1 wherein said particles are dyed or pigmented compositions carry an active ingredient selected from the group consisting of fragrances, vitamins, medicaments, botanical extracts and ultraviolet radiation absorbers.

3. The composition of claim 1 wherein said polyethylene comprises at least 10% by weight of said particles.

4. The composition of claim 2 wherein said polyethylene comprises at least 10% by weight of said particles.

5. The composition of claim 1 comprising said particles dispersed in a flowable continuous phase carrying medium that is not a solvent for said particles.

6. The composition of claim 2 comprising said particles dispersed in a flowable continuous phase carrying medium that is not a solvent for said particles.

7. The composition of claim 1 comprising said particles dispersed in a gel carrying medium that is not a solvent for said particles.

8. The composition of claim 2 comprising said particles dispersed in a gel carrying medium that is not a solvent for said particles.

9. A composition comprising solid particles comprising polyethylene, petrolatum and octyl palmitate, said solid particles carrying at least one active ingredient selected from the group consisting of fragrances, vitamins, medicaments, botanical extracts, cosmeceuticals and ultraviolet radiation absorbers, wherein the polyethylene, petrolatum and octyl palmitate are blended, or dissolued, in each other.

10. The composition of claim 9 wherein said particles are dyed or pigmented and carry an active ingredient selected from the group consisting of fragrances, vitamins, medicaments, botanical extracts, cosmeceuticals and ultraviolet radiation absorbers.

11. The composition of claim 1 wherein said solid particles comprise spheres.

12. The composition of claim 2 wherein said solid particles comprise spheres.

13. The composition of claim 9 wherein said solid particles comprise spheres.

14. The composition of claim 10 wherein said solid particles comprise spheres.

15. A method for moisturizing skin comprising the steps of:
 a. providing an emollient composition comprising polyethylene, petrolatum, and octyl palmitate, wherein the polyethylene, petrolatum and octyl palmitate are blended, or dissolved, in each other;
 b. applying an amount of the emollient to a portion of the skin; and
 c. working the emollient composition into the skin.

16. The method according to claim 15 wherein the emollient composition has a solid feel.

17. The method according to claim 16 wherein the solid feel emollient composition is in a generally spherical form.

18. The method according to claim 16 where the step of working the emollient composition into the skin is continued until the solid feel emollient composition has disappeared to the touch.

19. The method according to claim 17 where the step of working the emollient composition into the skin is continued until the solid feel emollient composition has disappeared to the touch.

20. The method according to claim 15 wherein the emollient composition is used in a cosmetic field selected from the group consisting of baby shampoos, baby lotions, baby oils, baby powders, baby creams, bath oils, bath tablets, bath salts, bubble baths, bath capsules, eye makeup, eyebrow pencils, eyeliners, eye shadows, eye lotions, eye makeup removers, mascara, fragrance preparations, colognes, toilet waters, perfumes, dusting powders, talcum powders, sachets, hair conditioners, hair sprays, hair straighteners, permanent waves, hair rinses (non-coloring), shampoos (non-coloring), hair tonics, hair dressings, wave sets, hair coloring preparations, hair dyes, hair colors, hair tints, hair rinses (coloring), hair color sprays, hair lighteners with color, hair bleaches, blushers, face powders, foundations, leg and body paints, lipsticks, makeup bases, rouges, makeup fixatives, manicuring basecoats, manicuring undercoats, cuticle softeners, hair creams, hair lotions, nail extenders, nail polishes, nail enamels, nail polish and enamel removers, oral hygiene products, dentifrices, bar soaps, detergents, deodorants, shaving preparations, aftershave lotions, beard softeners, men's talcum, preshave lotions, shave creams, shaving soaps, skin creams, skin lotions, skin powders, skin sprays, cold creams, cleansing lotions, cleansing liquids, cleansing pads, depilatories, face and neck scrubs, body and hand scrubs, leg and foot scrubs, foot powders, foot sprays, moisturizing creams, moisturizing lotions, night creams, paste masks, mud packs, skin fresheners, suntan gels, suntan creams, suntan liquids, indoor tanning preparations, and sunless tanning preparations. adiation absorbers.

* * * * *